United States Patent [19]

Herzig

[11] Patent Number: 5,250,647
[45] Date of Patent: Oct. 5, 1993

[54] ORGANOSILICON COMPOUNDS CONTAINING ALKENYL GROUPS, PROCESS FOR THEIR PREPARATION, AND USE OF THE SAME

[75] Inventor: Christian Herzig, Tachin am See, Fed. Rep. of Germany

[73] Assignee: Wacker-Chemie GmbH, Munich

[21] Appl. No.: 837,386

[22] Filed: Feb. 19, 1992

[30] Foreign Application Priority Data

Mar. 14, 1991 [DE] Fed. Rep. of Germany ....... 4108334

[51] Int. Cl.$^5$ ............................................. C08G 77/08
[52] U.S. Cl. ........................................ 528/15; 528/31; 528/25; 525/478; 556/445; 556/462
[58] Field of Search ..................... 528/15, 31; 556/445, 556/462; 525/478

[56] References Cited

U.S. PATENT DOCUMENTS

| | | | |
|---|---|---|---|
| 3,149,168 | 9/1964 | Karlan et al. | 568/673 |
| 3,271,362 | 9/1966 | Chalk et al. | 528/15 |
| 3,661,817 | 5/1972 | Hamilton et al. | 528/15 |
| 3,989,667 | 11/1976 | Lee et al. | 528/15 |
| 4,433,179 | 2/1984 | Lohse et al. | 568/664 |
| 4,503,208 | 3/1985 | Lin et al. | 528/15 |
| 4,609,574 | 9/1986 | Keryk et al. | 427/407.1 |
| 4,617,238 | 10/1986 | Crivello et al. | 428/452 |
| 5,113,006 | 5/1992 | Herzig | 556/453 |
| 5,118,772 | 6/1992 | Herzig et al. | 526/279 |

FOREIGN PATENT DOCUMENTS 046731 8/1981 European Pat. Off. .

OTHER PUBLICATIONS

Noll, Chemistry and Technology of Silicones, 1968, p. 392.

*Primary Examiner*—John C. Bleutge
*Assistant Examiner*—Margaret W. Glass

[57] ABSTRACT

Organosilicon compounds containing alkenyl groups and comprising average units of the formula $$A_a R_b Si(OR^1)_c O_{\frac{4-(a+b+c)}{2}} \quad (I)$$

in which R may be the same or different and are selected from monovalent hydrocarbon radicals having from 1 to 18 carbon atom(s) per radical and monovalent halogenated hydrocarbon radicals having from 1 to 18 carbon atom(s) per radical, $R^1$ may be the same or different and is selected from alkyl radicals having from 1 to 8 carbon atom(s) per radical and alkyl radicals having from 1 to 8 carbon atom(s) per radical, which are substituted by one or more ether oxygen atom(s), a is 0 or 1, with an average of from 0.003 to 1.0, b is 0, 1, 2 or 3, with an average of from 0.0 to 3.0, c is 0, 1, 2 or 3, with an average of from 0.0 to 3.0, and the sum $a+b+c \leq 4$, with an average of from 1.5 to 4.0, with the proviso that each molecule contains at least one radical A, and A is a radical of the formula $$(H_2C=CR^4CHR^3O(R^5O)_vH_{1-x}C=CH_{2-y}(R^2(OR^5)_wOCHR^3CR^4=CH_2)_y$$

in which $R^2$ is the same or different and is an alkylene radical having from 1 to 4 carbon atom(s), $R^3$ is the same or different and is a hydrogen atom or a methyl radical, $R^4$ is the same or different and is a hydrogen atom or a methyl or ethyl radical, $R^5$ is the same or different and is an alkylene radical having from 1 to 4 carbon atom(s), v is 0 or an integer and w is 0 or an integer, with the proviso that the radical A contains at least one spacer—$(R^5O)$—, and x is 0 or 1 and y is 0 or 1, with the proviso that the sum $x+y$ is 1 or 2.

9 Claims, No Drawings

ORGANOSILICON COMPOUNDS CONTAINING ALKENYL GROUPS, PROCESS FOR THEIR PREPARATION, AND USE OF THE SAME

The present invention relates to organosilicon compounds containing alkenyl groups and more particularly to a process for preparing organosilicon compounds containing alkenyl groups.

BACKGROUND OF THE INVENTION

According to U.S. Pat. No. 4,609,574 (published 2 September 1986, J R. Keryk et al., Dow Corning Corporation), organopolysiloxane compositions containing Si-bonded higher alkenyl groups, such as, for example 5-hexenyl groups, are more reactive than Si-bonded vinyl groups toward Si-bonded hydrogen. The organopolysiloxanes containing higher alkenyl groups can be prepared by reacting an organopolysiloxane containing Si-bonded hydrogen with an α, w-diene; however, multiple addition reactions always occur. The organopolysiloxanes containing higher alkenyl groups are therefore preferably obtained from the corresponding silanes by reacting an α, w-diene in a large excess with a silane containing Si-bonded hydrogen and subsequently hydrolyzing the silane and equilibrating the silane with an organopolysiloxane.

E. Lukevits et al., Zhurnal Obshchei Khimii, Vol. 56, 140-143, 1986 (Chemical Abstracts, Vol. 105, 226720 h, 1986) describe the hydrosilylation of alkenes and alkynes using dimethyl(2-thienyl)silane. The triple bond is more reactive than the double bond.

In M. G. Voronkov, Irk, Inst. Org. Khim., 55(9), 2091-3 (Chemical Abstracts, Vol. 105, 97545d, 1986), the reaction of 1-allyloxy-3-propargyloxy-2-propanol with trialkylsilanes is described, in which yields of up to 70% have been achieved.

In M. Licchelli, A. Greco, Tetrahedron Lett. 28 (1987) 3719-22 the hydrosilylation of 2-methyl-1-buten-3-yne using methylchlorosilanes is described, in which the hydrosilylation of the conjugated alkenyne results in both the mono- and di-addition of the silanes.

In M. G. Veliev, Azerb, Khim, Zh. 1987 (1) 60-4 (Chemical Abstracts, Vol. 110, 135304n), the reaction of a silane with an organic compound which has both a carbon-carbon double bond and a triple bond is described, in which the organic compound contains an epoxy or a cyano group.

The German application P 3935775.9 (application date 27 October 1989, Wacker-Chemie GmbH) and the corresponding US application 1990) now U.S. Pat No. 5,113,006 disclose that organosilicon compounds containing alkenyl groups in which the individual carbon-carbon double bonds within a molecular moiety are relatively close to each other, have an inhibiting effect in a reaction with Si-bonded hydrogen.

Therefore, it is an object of the present invention to provide a process for selectively preparing organosilicon compounds containing alkenyl groups. A further object of the present invention is to provide organosilicon compounds containing alkenyl groups which are prepared by a simple process.

SUMMARY OF THE INVENTION

The foregoing objects and others which will become apparent from the following description are accomplished in accordance with this invention, generally speaking, by providing organosilicon compounds containing alkenyl groups and comprising average units of the formula $$A_a R_b Si(OR^1)_c O_{\frac{4-(a+b+c)}{2}} \quad (I)$$

in which the R radicals may be the same or different and are monovalent hydrocarbon radicals or monovalent halogenated hydrocarbon radicals having from 1 to 18 carbon atom(s) per radical, the $R^1$ radicals may be the same or different and are alkyl radicals having from 1 to 8 carbon atom(s) per radical, which may be substituted by one or more ether oxygen atom(s), a is 0 or 1, with an average of from 0.003 to 1.0, b is 0, 1, 2 or 3, with an average of from 0.0 to 3.0, c is 0, 1, 2 or 3, with an average of from 0.0 to 3.0, and the sum $a+b+c \leq 4$, with an average of from 1.5 to 4.0, with the proviso that each molecule contains at least one radical A, and A is a radical of the formula $$(H_2C=CR^4CHR^3O(R^5O)_vR^2)_x \overset{|}{H}_{1-x}C=CH_{2-y}(R^2(OR^5)_wOCHR^3CR^4=CH_2)_y$$

in which $R^2$ may be the same or different and is an alkylene radical having from 1 to 4 carbon atom(s), $R^3$ may be the same or different and is a hydrogen atom or a methyl radical, $R^4$ may be the same or different and is a hydrogen atom, methyl or ethyl radical, $R^5$ may be the same or different and is an alkylene radical having from 1 to 4 carbon atom(s), v is 0 or an integer and w is 0 or an integer, with the proviso that the radical A contains at least one spacer group —($R^5O$)—, and x is 0 or 1 and y is 0 or 1, with the proviso that the sum x+y is 1 or 2.

The invention also relates to a process for preparing organosilicon compounds containing alkenyl groups, which comprises reacting an organic compound (1) of the formula $$(H_2C=CR^4CHR^3O(R^5O)_vR^2)_xH_{1-x}C\equiv CH_{1-y}(R^2(OR^5)_wOCHR^3CR^4=CH_2)_y \quad (1)$$

in which x, y, v and z are the same as above, with the proviso that the sum x+y is 1 or 2 and that compound (1) contains at least one spacer group —($R^5O$)—, and $R^2$, $R^3$, $R^4$ and $R^5$ in each case may be the same or different and are the same as above, with an organosilicon compound (2) containing at least one Si-bonded hydrogen atom in its molecule, in the presence of a catalyst (3) which promotes the addition reaction of Si-bonded hydrogen with an aliphatic multiple bond.

DESCRIPTION OF THE INVENTION

The organosilicon compounds of this invention are preferably silanes or organopolysiloxanes.

The organosilicon compounds of this invention preferably have an average molecular weight of from 200 to 100,000 g/mol, and more preferably from 214 to 10,000 g/mol, and more preferably have a viscosity of from 1 to 1,000,000 mm$^2$·s$^{-1}$ at 25° C., and more preferably from 1 to 20,000 mm$^2$·s$^{-1}$ at 25° C.

Examples of radicals represented by R are alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals, such as the n-heptyl radical, octyl radicals, such as the n-octyl radical, and isooctyl radicals, such as the 2, 2, 4-trimethylpentyl radical, nonyl radicals, such as the n-nonyl radical, decyl radicals, such as the n-decyl radical, dodecyl radicals, such as the n-dodecyl radical, and octa- —$(CH_2)_4$. $R^2$ is preferably the —$CH_2$—group. The radicals $R^3$ and $R^4$ are preferably hydrogen atoms.

Examples of radicals represented by $R^5$ are —$(CH_2)_2$—, —$(CH_2)_3$—, —$(CH_2)_4$—, —$CH_2CH(CH_3)$— and —$(CH_2)_2CH(CH_3)$—in which $R^5$ is preferably the —$(CH_2)$— group. The sum of x and y is preferably 1. v and w are each preferably integers of from 1 to 20, and more preferably from 1 to 4.

Examples of radicals represented by A are those of the formula

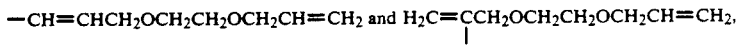

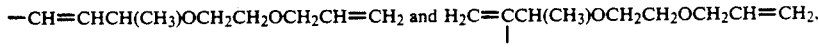

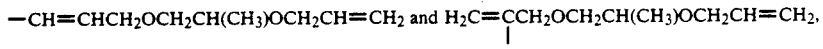

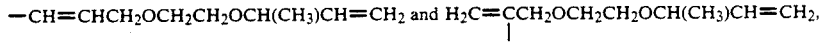

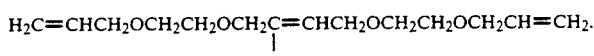

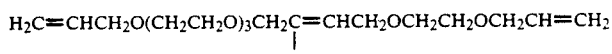

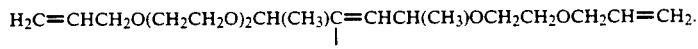

and

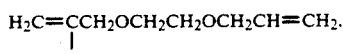

decyl radicals, such as the n-octadecyl radical; cycloalkyl radicals, such as cyclopentyl, cyclohexyl and cycloheptyl radicals, and methylcyclohexyl radicals; aryl radicals, such as the phenyl, naphthyl, anthryl and phenanthryl radicals; alkaryl radicals, such as o-, m-and p-tolyl radicals, xylyl radicals and ethylphenyl radicals; and aralkyl radicals, such as the benzyl radical and the α- and β-phenylethyl radical.

Examples of halogenated radicals represented by R are haloalkyl radicals, such as the 3, 3, 3-trifluoro-n-propyl radical, the 2, 2, 2, 2′,2′,2′-hexafluoroisopropyl radical and the heptafluoroisopropyl radical, and haloaryl radicals, such as the o-, m-and p-chlorophenyl radicals.

The R radicals are preferably hydrocarbon radicals having from 1 to 6 carbon atom(s), and more preferably methyl radicals.

Examples of $R^1$ radicals are the examples of the alkyl radicals having from 1 to 8 carbon atom(s) recited for the R radical, and also the methoxyethyl and ethoxyethyl radicals. The $R^1$ radicals are preferably ethyl and methyl radicals.

Examples of alkylene radicals represented by $R^2$ are those of the formula —$(CH_2)$—, —$CH(CH_3)$—, —$C(CH_3)_2$—, —$C(CH_3)(C_2H_5)$—, —$(CH_2)_2$—and The radicals A are preferably —CH=CHCH$_2$OCH$_2$CH$_2$OCH$_2$CH=CH$_2$ and

and

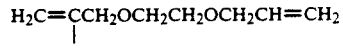

in which the isomeric pair —CH=CHCH$_2$OCH$_2$CH$_2$OCH$_2$CH=CH$_2$ or

is especially preferred.

Preferred silanes containing alkenyl groups are those of the formula $$AR_dSi(OR^1)_{-d} \qquad (II)$$

in which A, R and $R^1$ are the same as above, and d is 0, 1 or 2.

Preferred organopolysiloxanes containing alkenyl groups are those of the formula $$A_gR_{3-g}SiO(SiR_2O)_n(SiRAO)_mSiR_{3-g}A_g \qquad (III)$$

in which A and R are the same as above, g is 0 or 1, n is 0 or an integer of from 1 to 1,500, and m is 0 or an integer of from 1 to 100, with the proviso that each molecule contains at least one radical A.

Examples of organic compounds (1) which are employed in the process of this invention are those of the formula $HC\equiv CCH_2OCH_2Ch_2OCH_2CH=CH_2$, $HC\equiv CCH(CH_3)OCH_2CH_2OCH_2CH=CH_2$, $HC\equiv CCH_2OCH_2CH(CH_3)OCH_2CH=CH_2$, $HC\equiv CCH_2OCH_2CH_2OCH(CH_3)CH=CH_2$, $HC\equiv CCH_2O(CH_2CH_2O)_2CH_2CH=CH_2$, $H_2C=CHCH_2OCH_2CH_2OCH_2C\equiv CCH_2OCH_2CH_2OCH_2CH=CH_2$, $H_2C=CHCH_2O(CH_2CH_2O)_3CH_2C\equiv CCH_2OCH_2CH_2OCH_2CH=CH_2$ ol and $H_2C=CHCH_2O(CH_2CH_2O)_2CH(CH_3)C\equiv CCH(CH_3)OCH_2CH_2OCH_2CH=CH_2$.

Processes for the preparation of the organic compounds (1) are described in EP-B 46,731 (published 3 October 1984, F. Lohse et al., Ciba-Geigy AG).

The organosilicon compound (2) containing at least one Si-bonded hydrogen atom per molecule is preferably a silane containing one Si-bonded hydrogen atom per molecule or an organopolysiloxane containing at least one Si-bonded hydrogen atom per molecule, comprising units of the formula $$H_eR_fSiO_{\frac{4-(e+f)}{2}} \qquad (IV)$$

in which R is the same as above, e is 0 or 1, with an average of from 0.003 to 1.0, f is 0, 1, 2 or 3, with an average of from 0.0 to 3.0, and the sum of e+f is not greater than 3.

The organopolysiloxanes containing at least one Si-bonded hydrogen atom preferably contain at least 0.04% by weight, and more preferably from 0.1 to 1.6% by weight, of Si-bonded hydrogen, and their average viscosity is preferably from 2 to 20,000 $mm_2 \cdot s^{-1}$ at 25° C.

The silanes containing one Si-bonded hydrogen atom per molecule are preferably those of the formula $$HR_dSi(OR^1)_{3-d} \qquad (V),$$

in which R, $R^1$ and d are the same as above.

The organopolysiloxanes containing at least one Si-bonded hydrogen atom per molecule are preferably those of the formula $$H_gR_{3-g}SiO(SiR_2O)_n(SiRHO)_mSiR_{3-g}H_g \qquad (VI),$$

in which R, g, n and m are the same as above.

A preferred example of a silane of formula (V) is triethoxysilane. Preferred examples of organopolysiloxanes of formula (VI) are copolymers comprising dimethylhydrogensiloxane and dimethylsiloxane units, copolymers comprising dimethylhydrogensiloxane, dimethylsiloxane and methylhydrogensiloxane units, copolymers comprising trimethylsiloxane and methylhydrogensiloxane units, and copolymers comprising trimethylsiloxane, dimethylsiloxane and methylhydrogensiloxane units.

Processes for the preparation of organopolysiloxanes containing at least one Si-bonded hydrogen atom per molecule, including those of the preferred type, are generally known.

In the process of this invention, the organic compound (1) is preferably used in such amounts that from 1 to 2 mols, preferably from 1.05 to 1.20 mols, of the organic compound (1) are present per gram-atom of Si-bonded hydrogen in the organosilicon compound (2).

In the process of this invention, the catalysts, (3), which promote the addition reaction of Si-bonded hydrogen with an aliphatic multiple bond may also be the same catalysts which have been or could have been employed heretofore to promote the addition reaction of Si-bonded hydrogen with an aliphatic multiple bond. The catalyst (3) is preferably a metal from the platinum metal group or a compound or a complex from the platinum metal group. Examples of catalysts of this type are metallic and finely divided platinum, which may be supported on carriers, such as silicon dioxide, aluminum oxide or activated charcoal, compounds or complexes of platinum, such as platinum halides, for example $PtCl_4$, $H_2PtCl_6 \cdot 6H_2O$, $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including products of the reaction of $H_2PtCl_6 \cdot 6H_2O$ and cyclohexanone, platinum-vinylsiloxane complexes, such as platinum-1, 3-divinyl-1, 1, 3, 3-tetramethyldisiloxane complexes, containing or are free of detectable inorganically bonded halogen, bis(gammapicoline)platinum dichloride, trimethylenedipyridine platinum dichloride, dicyclopentadiene platinum dichloride, (dimethylsulfoxide)ethyleneplatinum (II) dichloride, and products of the reaction of platinum tetrachloride with an olefin and a primary amine or a secondary amine or a primary amine and a secondary amine, as in U.S. Pat. No. 4,292,434, such as the product of the reaction of platinum tetrachloride dissolved in 1-octene with sec-butylamine, or ammonium-platinum complexes as in EP-B 110,370.

The catalyst (3) is preferably employed in amounts of from 0.5 to 200 ppm by weight (parts by weight per million parts by weight), and more preferably in amounts of from 1 to 50 ppm by weight, calculated as elemental platinum and based on the total weight of the organic compound (1) and the organosilicon compound (2).

The process of this invention is preferably carried out under the pressure of the ambient atmosphere, i.e., at about 1020 hPa (abs.), but may also be carried out at elevated or reduced pressures. The process according to the invention is furthermore preferably carried out at a temperature of from 80° C. to 150° C., more preferably from 100° C. to 150° C., and more particularly from 120° C. to 130° C.

In the process of this invention, organic solvents which are inert towards the reactants may also be used, although the additional use of an organic solvent which is inert towards the reactants is not preferred. Examples of organic solvents which are inert towards the reactants are toluene, xylene, octane isomers and butyl acetate.

Excess organic compound (1) and any organic solvent which is inert towards the reactants are preferably removed by distillation from the organosilicon compounds containing alkenyl groups prepared by the process of this invention. If it is desired to separate this from excess organic compound (1), further separation steps, such as, for example, extraction with water or alcohols, may be necessary in certain circumstances, depending on the molecular weight of the organic compound (1), and in particular if v and/or w have large values.

The process of this invention has the advantage that organosilicon compounds having alkenyl groups can be prepared in very high selectivity and also in a very high yield.

The addition reaction of the organosilicon compound (2) containing at lease one Si-bonded hydrogen atom per molecule with the organic compound (1) takes place, both for $x=0$ and $y=1$ and for $x=1$ and $y=0$, selectively at the terminal triple bond and not at the terminal double bond, and for $x=1$ and $y=1$ selectively at the internal triple bond and not at the terminal double bonds. Thus, organopolysiloxanes containing alkenyl groups can be prepared directly from organopolysiloxanes containing Si-bonded hydrogen atoms and the organic compound (1) without crosslinking occurring via the terminal double bonds. In addition, organosilicon compounds containing alkenyl groups are obtained according to this invention without double bond isomerization of the terminal double bond(s) from the end position into the chain taking place. However, should double bond isomerization occur under certain conditions, such as, for example, under the influence of strong bases, the organosilicon compounds of this invention have the advantage that the presence of the spacer precludes a Claisen rearrangement as a thermal secondary reaction.

The organosilicon compounds containing alkenyl groups of this invention have the advantage that they are very suitable for hydrosilylation reactions, because they show only a relatively small inhibiting effect, or none at all, due to the presence of the spacer between the individual double bond.

The organosilicon compounds containing alkenyl groups which are present after completion of the 1st step and optionally equilibrated with organopolysiloxanes (4) which are preferably selected from the group comprising linear organopolysiloxanes containing terminal triorganosiloxy groups, of the formula

in which $R^6$ may be the same or different and is the same as R above and r is 0 or an integer having a value of from 1 to 1,500, linear organopolysiloxanes containing terminal hydroxyl groups, of the formula

in which $R^7$ may be the same or different and is the same as R above, and s is an integer having a value of from 1 to 1,500, cyclic organopolysiloxanes of the formula

in which $R^8$ may be the same or different and is the same as R above, and t is an integer from 3 to 12, and copolymers comprising units of the formula

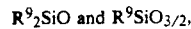

in which $R^9$ may be the same or different and is the same as R above.

The mixing ratios of the organopolysiloxanes employed in the 2nd step of the process of this invention, which may be carried out, if necessary, are determined merely by the desired proportion of alkenyl groups in the organopolysiloxanes produced in the 2nd step of the process of this invention and by the mean chain length desired.

In the equilibration carried out, if necessary, in the 2nd step of the process of this invention, basic catalysts which promote the equilibration are preferably employed. Examples of such catalysts are alkali metal hydroxides, such as sodium hydroxide and potassium hydroxide, trimethylbenzylammonium hydroxide and tetramethylammonium hydroxide, in which alkali metal hydroxides are preferred.

Alkali metal hydroxides are preferably used in amounts of from 50 to 10,000 ppm (parts per million) by weight, and more preferably from 500 to 2,000 ppm by weight, based on the total weight of the organosilicon compounds employed. Although the use of acidic equilibration catalysts is possible, it is not preferred.

The equilibration carried out, if necessary, in the 2nd step of the process of this invention is preferably carried out at from 80° C. to 150° C. and at the pressure of the ambient atmosphere, i.e., at about 1020 hPa (abs.). If desired, however, higher or lower pressures can also be used. The equilibration is preferably carried out in from 5 to 20% by weight, based on the total weight of the organosilicon compounds employed in each case, in water-immiscible solvents, such as toluene. The catalyst can be deactivated before the mixture obtained on equilibration is further processed.

The various steps of the process of this invention can be carried out successively in one and the same reaction vessel or in separate reaction vessels. The steps are preferably carried out successively in one and the same reaction vessel. The process of this invention can be carried out batchwise, semicontinuously or continuously.

If the organosilicon compounds of this invention have $OR^1$ groups, in which $R^1$ is the same as above, and contain alkenyl groups, they may be subjected to hydrolysis and/or condensation. Hydrolysis and condensation reactions of organosilicon compounds having organyloxy groups are already widely known. For example, the organosilicon compounds of this invention may be reacted with linear or cyclic organosilicon compounds containing hydroxyl groups, such as, for example, α, w-dihydroxydimethylpolysiloxane, in the presence of a catalyst, such as, for example, organotin compounds, esters of titanium and zirconium, quaternary nitrogen bases and mineral acids, and if appropriate in the presence of a solvent. Hydrolysis and condensation are thus preferably carried out at between 23° and 150° C., and more preferably between 60 and 120° C., and at a pressure of between 900 and 1110 hPa.

The organopolysiloxanes of this invention containing alkenyl groups may be crosslinked, just like the organopolysiloxanes containing Si-bonded vinyl groups, using organopolysiloxanes containing Si-bonded hydrogen in the presence of hydrosilylation catalysts.

The organosilicon compounds of this invention may, for example, be used in compositions which contain (A) an organosilicon compound of the formula (I), preferably of formula (III), which contains alkenyl groups, (B) an organopolysiloxane which contains at least one Sibonded hydrogen atom, and (C) a catalyst which promotes the addition reaction of Si-bonded hydrogen with an aliphatic multiple bond.

Component (B) is preferably an organopolysiloxane of formula (IV), and more preferably of formula (VI).

Component (C) is preferably one of the above-mentioned catalysts (3).

In addition, the compositions of this invention may contain additional substances (D), such as, for example, agents which retard the addition reaction of Si-bonded hydrogen with an alipha15 tic multiple bond at room temperature. Such inhibitors are described, for example, in U.S. Pat. No. 3,933,880. Examples of these are acetylenically unsaturated alcohols, such as 3-methyl-1-butyn-3-ol, 1-ethynylcyclohexan-1-ol, 3, 5-dimethyl-1-hexyn-3-ol, 3-methyl-1-pentyn-3-ol and the like.

Compositions which contain the silicon compounds of this invention containing alkenyl groups are suitable for preparing adhesive-repellent coatings, tack-free top coats, rubber-like coatings or moldings and encapsulation compositions.

In the examples described below, all viscosity data is determined at a temperature of 25° C. Unless otherwise specified, the examples below are carried out at the pressure of the ambient atmosphere, i.e., at about 1,000 hPa, and at room temperature, i.e., at about 23° C., or at a temperature which is produced on combination of the reactants at room temperature without additional heating or cooling.

EXAMPLE 1

(I) About 795 g of 2-propynoxyethanol (commercially available under the name Golpanol PME from BASF) are stirred at 42° C. for 2 hours with 1,200 g of 50% by weight NaOH, 705 g of allyl chloride and 21 g of trimethylbenzylammonium chloride. As soon as the initial exothermic reaction has subsided, the temperature of the mixture is held under reflux at the boiling point with vigorous stirring with the aid of a warm water bath. The reflux temperature reaches about 65° C. After cooling, 1,200 ml of water are added, and the lower phase is subsequently separated off. The crude product thus obtained is washed twice with 300 ml of water in each case and distilled in vacuo. About 940 g of a colorless distillate are obtained at 50° C. to 100° C. and 5 hPa (abs.). According to the $^1$H-NMR spectrum, it has the average composition HC≡CCH$_2$O(CH$_2$CH$_2$O)$_{1.13}$CH$_2$CH=CH$_2$ with a C≡C equivalent of 145.7.

About 153 g of allyl ether (1.05 mol of —C≡C—), whose preparation is described in (I) above, are mixed with 2 mg of platinum as a 1% by weight solution of H$_2$PtCl$_6$ in isopropanol. The mixture is warmed to 120° C. under nitrogen, and a total of 164 g of triethoxysilane (1.00 mol) are subsequently added dropwise over a period of 2 hours. After a reaction time of 4 to 5 hours, alkaline determination of hydrogen indicates a conversion of more than 99% of the Sibonded hydrogen in the triethoxysilane. The crude product thus obtained contains less than 3% by weight of allyl ether starting material. According to the $^1$H-NMR spectrum, the ratio between the

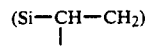

groups and the

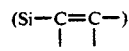

groups is 52:1. Vacuum distillation at from 110° C. to 160° C. at 5 hPa (abs.) gives 270 g of a colorless liquid having a viscosity of 2.6 mm$^2$/s, of the average formula pti

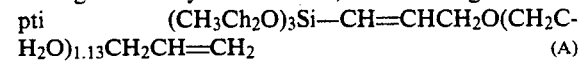

and

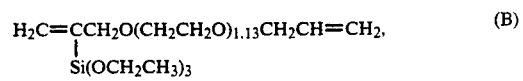

the molar A:B ratio is 43:57.

| $^{29}$Si-NMR spectrum: | δ = −57.8 ppm | (A) |
|---|---|---|
| (C$_6$D$_6$) | −60.0 ppm | (B) |
| $^1$H-NMR spectrum: | δ = 5.72 ppm (dtr, 1H, SiC<u>H</u>=CH), | (A) |
| (CDCL$_3$) | | |
| | 6.47 ppm (dtr, 1H, SiC=C<u>H</u>—H). | |
| | δ = 5.76 ppm (dtr, 1H, SiC=<u>C</u>H), | (B) |
| | 6.01 ppm (dtr, 1H, SiC=<u>C</u>H). | |

EXAMPLE 2

About 50 g of the product prepared in Example 1 are mixed at a temperature of 90° C. with 140 g of a 75% by weight solution of a phenylmethylsiloxane containing 3% by weight of Si-bonded hydroxyl groups, and having a molar ratio between Si-bonded phenyl groups and Si-bonded methyl groups of 37:63 and a viscosity of 90 mm$^2$/s in xylene, and 0.1 ml of HClO$_4$. The mixture is stirred and after 3 hours, 1 g of sodium bicarbonate is added with agitation. The mixture is allowed to cool and then filtered. After the xylene and the ethanol formed have been removed by distillation (60° C./5 hPa, abs.), 135 g of a double bond-containing resin having a viscosity of 4,000 mm$^2$/s and an iodine number of 45 are obtained. Accordingly, 564 g of resin contain precisely 1.00 mol of aliphatic double bonds.

EXAMPLE 3

About 77 g of allyl ether (0.53 mol of —C≡C—), whose preparation is described in Example 1 (I) above, are warmed to 120° C. under nitrogen, and a mixture of 127 g of an α, w-dihydrogendimethylpolysiloxane, containing 0.394% by weight of Si-bonded hydrogen, and 2 mg of platinum as a 1% by weight solution of platinum tetrachloride in 1-octene is subsequently added dropwise over a period of 2 hours. After a reaction time of 1.5 hours, alkaline determination of hydrogen indicates a conversion of more than 99% of the Sibonded hydrogen in the α, w-dihydrogendimethylpolysiloxane. Removal of the volatile constituents at 120° C. and 10$^3$ hPa gives 170 g of a clear yellowish oil having a viscosity of 13.5 mm$^2$/s and an iodine number of 112. According to the $^1$H-NMR spectrum, the resultant dimethylpolysiloxane contains one Si-bonded radical of the average formula

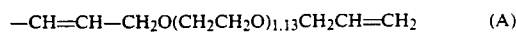

or $H_2C=C-CH_2O(CH_2CH_2O)_{1.13}CH_2CH=CH_2$ (B)
|
in each of the terminal units and has a mean chain length of 16, and the molar A:B ratio is 45:55. The ratio, likewise determined from the $^1$H-NMR spectrum, between the (Si—C≡C—)
| | groups and the

| $^{29}$Si-NMR spectrum: | $\delta = -3.1$ ppm | (B) |
|---|---|---|
| (C$_6$D$_6$) | (2 Si) | |
| | $-3.7$ ppm | (A) |
| | $-20.2$ to $-22.4$ ppm (14 Si, —SiMe$_2$O—) | |

(Si—CH—CH$_2$)
| groups of 300:1 clearly shows the preference of the triple bond over the double bond. A shift of the allylic terminal double bond to the ether oxygen is not observed.

| $^{29}$Si-NMR spectrum: | $\delta = -3.1$ ppm | (B) |
|---|---|---|
| (C$_6$D$_6$) | (2 Si) | |
| | $-3.7$ ppm | (A) |
| | $-20.2$ to $-22.4$ ppm (14 Si, —SiMe$_2$O—) | |

EXAMPLE 4

About 20 g of the product prepared in Example 3 are mixed with 300 g of α, w-dihydroxypolydimethylsiloxane having a viscosity of 20,000 mPa.s, 100 ppm of PNCl$_2$ in a 30% by weight solution of 1, 1, 1-trichloroethane are added, and the mixture is equilibrated at 120° C. A check of the viscosity shows that the siloxane mixture has fully reacted in less than 1 hour. After filtration through magnesium oxide and heating at 120° C. and 2 hPa, 290 g of a yellowish oil having a viscosity of 800 mm$^2$/s are obtained. The iodine number of 6.6 indicates a calculated mean chain length of 204 Si units.

EXAMPLE 5

About 120 g of allyl ether (0.82 mol of —C≡C—), whose preparation is described in Example 1 (I), are warmed to 120° C. under nitrogen with 7 mg of platinum as a 1% by weight solution of platinum tetrachloride in 1-octene. An equilibrate of dimethylsiloxane, methylhydrogensiloxane and dimethylhydrogensiloxane units having a viscosity of 70 mm$^2$/s and containing 0.133% by weight of Si-bonded hydrogen is subsequently metered in over a period of 3 hours. After a reaction time of 5 hours, an alkaline determination of hydrogen indicates a conversion of more than 99% of the Si-bonded hydrogen of the equilibrate. Removal of the excess allyl ether starting material at 120° C. and 10$^{-3}$ hPa gives a clear, yellowish liquid having a viscosity of 210 mm$^2$/s and an iodine number of 51. According to the $^1$H-NMR spectrum, the ratio between the (Si—C≡C—)
| | groups and the (Si—CH—CH$_2$)
| groups is greater than 200:1. The organopolysiloxane thus obtained contains an average of

—CH=CH—CH$_2$O(CH$_2$CH$_2$O)$_{1.13}$CH$_2$CH=CH$_2$ (A)

or $H_2C=C-CH_2O(CH_2CH_2O)_{1.13}CH_2CH=CH_2$ (B)
| as terminal and also as lateral groups and has a mean chain length between 70 and 80, in which the A:B ratio is 39:61. $^1$H-NMR spectrum (CDCl$_3$) terminal groups:

| $\delta = 5.61$ ppm (m, 1H) | (B). |
|---|---|
| (SiC=CH$_2$) | |
| 5.88 ppm (m, 1H) | |
| 6.25 ppm (dtr, 1H, SiCH=C$\underline{H}$) | (A) | lateral groups:

| $\delta = 5.67$ ppm (m, 1H) | (B). |
|---|---|
| (SiC=CH$_2$) | |
| 5.91 ppm (m, 1H) | |
| 6.30 ppm (dtr, 1H, SiCH=C$\underline{H}$) | (A). |

Double bond isomerization of allyloxy to 1-propenyloxy cannot be observed.

EXAMPLE 6

(II) About 1,200 g of 50% by weight NaOH are mixed with vigorous stirring with 690 g of ethoxylated 2-butyne-1, 4-diol (commercially available under the name Golpanol BEO from BASF) corresponding to 3.75 mol of —C≡C—, 820 g of allyl chloride and 21 g of trimethylbenzylammonium chloride. The heat of reaction resulted in gentle boiling. The mixture is then heated under reflux until the reflux temperature reaches about 65° C. The mixture is cooled, and 1,200 ml of water are added with stirring, after which the mixture separates into two clear phases. The aqueous phase is discarded, and the crude product is washed twice with 300 ml of water in each case. Excess allyl chloride is removed by distillation, and the allyl ether is removed in vacuo (11 hPa, abs.) at between 110° C. and 160° C. About 916 g of a colorless distillate having an iodine number of 286 are obtained. The $^1$H-NMR spectrum indicates an average composition of CH$_2$=CHCH$_2$(OCH$_2$CH$_2$)$_{1.02}$OCH$_2$C≡CC-H$_2$O(CH$_2$CH$_2$O)$_{1.02}$CH$_2$CH=CH$_2$ which corresponds to a C≡C equivalent of 255.8 g. About 3.5 mg of platinum tetrachloride in 1-octene are dispersed in 139 g of diallyl ether, whose preparation is described in (II) above, and the mixture is warmed to 130° C. under nitrogen. About 227 g of an α, w-dihydrogenpolydimethylsiloxane having a viscosity of 7 mm$^2$/s are added dropwise over a period of 1.5 hours, the temperature of the reaction mixture being held between 125° C. and 130° C. After a reaction time of 3 hours, alkaline determination of hydrogen indicates a conversion of more than 99% of the Si-bonded hydrogen of the organopolysiloxane. Removal of volatile constituents at 120° C. and 2 hPa gives 340 g of a clear yellow oil having an iodine number of 134 and a viscosity of 30 mm²/s. The oil still contains 2% by weight, based on the total weight of the oil, of the diallyl ether employed in excess. According to the ¹H-NMR spectrum, the dimethylpolysiloxane thus obtained contains one Si-bonded radical of the average formula

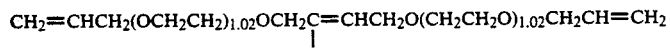

in each of the terminal units and has a mean chain length of 15. The ¹H-NMR spectrum also indicates that the ratio between the

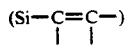

groups and the

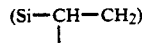

groups is 70:1.

| ¹H-NMR spectrum: (CDCl₃) | δ = 6.06 ppm (tr, 1H, —O—CH₂—CH=C—Si) |
|---|---|

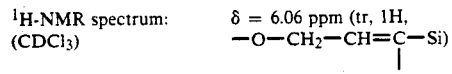

EXAMPLE 7

About 67 g of the product prepared in Example 6 are blended with 670 g of octamethylcyclotetrasiloxane. About 2.0 g of fresh 40% KOH solution in methanol are added, and the mixture is equilibrated at 150° C. for 4 hours. During cooling, 1.0 g of glacial acetic acid is added, and the mixture is then stirred for 0.5 hour with 8 g of slightly acidic alumina. After filtration, volatile, cyclic compounds are removed at 100° C. in vacuo (2 hPa). About 600 g of a yellowish oil having a viscosity of 1,290 mm²/s and an iodine number of 7 are obtained. This corresponds to a mean chain length of about 285 Si units.

EXAMPLE 8

About 100 g of the product prepared in Example 5 are mixed with 300 g of octamethylcyclotetrasiloxane, then with 1.0 g of a fresh 40% KOH solution in methanol and the mixture is heated at 150° C. for 5 hours. During cooling, the catalyst is neutralized using 0.5 g of glacial acetic acid. About 4 g of slightly acidic alumina are added and the mixture is filtered to give a clear solution. After the volatile constituents are removed at 100° C. in vacuo (2 hPa), a yellowish oil having a viscosity of 1,140 mm²/s is obtained. At an iodine number of 12, approximately each 50th Si atom of the polydimethylsiloxane chain carried the side chain A or B described in Example 5.

EXAMPLE 9

A mixture is prepared from 20.0 g of the product prepared in Example 4, 30 mg of 2-methyl-3-butyn-2-ol, 200 mg of a platinum catalyst solution (commercially available under the name "Lüsung OL" from Wacker-Chemie GmbH) and 400 mg of a hydrolysate having a viscosity of 20 mm²/s made from methyldichlorosilane and trimethylchlorosilane. A glass rod is used to coat low-absorption glassine paper with this mixture at a coating thickness of 2 to 3 μm, and the coating is allowed to crosslink in a circulating-air oven preheated to 80° C. After 8 seconds, the coating is tack-free and abrasion-resistant. The pot life is 20 hours. Under the same identical conditions, except that the 2-methyl-3-butyn-2-ol is omitted, a tack-free, abrasion-resistant coating is obtained after only 5 seconds. The pot life in this case is only 10 minutes.

EXAMPLE 10

(III) About 90 g of a phenylmethylpolysiloxane containing 14% by weight of Si-bonded methoxy groups (available under the trade name SY 231 from Wacker-Chemie GmbH) are equilibrated for 3 hours with vigorous boiling with 98 g of 3-mercaptopropyltrimethoxysilane, 3 g of glacial acetic acid and 10 ml of water. The volatile constituents are then removed by distillation at 80° C. and 5 hPa. About 162 g of a clear colorless liquid having a viscosity of 140 mm²·s⁻¹ are obtained. About 5.6 g of the product prepared in Example 2 are mixed with 3.3 g of the 3-mercaptopropylfunctional phenylmethyl resin described in (III) above, and 0.2 g of a free-radical initiator (commercially available under the name Darocure 1173 from Merck, Darmstadt), and sufficient xylene is added so that a processing viscosity of about 500 mm²/s is obtained. A mercury medium-pressure lamp having a power of 80 watts/cm of lamp length cures a coating of the above mixture, applied thinly (5 μm) to paper, in less than one second to give a tack-free, abrasion-resistant coating.

What is claimed is:

1. An organosilicon compound containing alkenyl groups and having average units of the formula

in which R is selected from the group consisting of monovalent hydrocarbon radicals having from 1 to 18 carbon atom(s) per radical and monovalent halogenated hydrocarbon radicals having from 1 to 18 carbon atom(s) per radical, R¹ is selected from the group consisting of alkyl radicals having from 1 to 8 carbon atom(s) per radical and alkyl radicals having from 1 to 8 carbon atom(s) per radical which are substituted by one of more ether oxygen atom(s), a is 0 or 1, with an average of from 0.003 to 1.0, b is 0, 1, 2 or 3, with an average of from 0.0 to 3.0, c is 0, 1, 2 or 3, with an average of from 0.0 to 3.0, with the proviso that each molecule contains at least one radical A, where A is a radical of the formula $(H_2C=CR^4CHR^3O(R^5O)_vR^2)_xH_{1-x}C=$ $=CH_{2-y}(R^2(OR^5)_wOCHR^3CR^4=CH_2)_y$ in which $R^2$ is an alkylene radical having from 1 to 4 carbon atom(s), $R^3$ is selected from the group consisting of a hydrogen atom and a methyl radical, $R^4$ is selected from the group consisting of a hydrogen atom, a methyl radical and an ethyl radical, $R^5$ is an alkylene radical having from 1 to 4 carbon atom(s), v is 0 or an integer and w is 0 or an integer, with the proviso that the radical A contains at least one spacer $—(R^5O)—$, and x is 0 or 1 and y is 0 or 1, with the proviso that the sum $x+y$ is 1 or 2.

2. The organosilicon compound of claim 1, which is a silane or an organopolysiloxane.

3. The organosilicon compound of claim 1, which is a silane of the formula $$AR_dSi(OR^1)_{3-d} \quad (II)$$

in which R is selected from the group consisting of monovalent hydrocarbon radicals having from 1 to 18 carbon atom(s) per radical and monovalent halogenated hydrocarbon radicals having 1 to 18 carbon atom(s) per radical, $R^1$ is selected from the group consisting of alkyl radicals having from 1 to 8 carbon atom(s) per radical and alkyl radicals having from 1 to 8 carbon atom(s) per radical which are substituted by one or more ether oxygen atom(s), d is 0, 1 or 2 and A is a radical of the formula $(H_2C=CR^4CHR^3O(R^5O)_vR^2)_xH_{1-x}C=$ $=CH_{2-y}(R^2(OR^5)_wOCHR^3CR^4=CH_2)_y$ in which $R^2$ is an alkylene radical having from 1 to 4 carbon atom(s), $R^3$ is selected from the group consisting of a hydrogen atom and a methyl radical, $R^4$ is selected from the group consisting of a hydrogen atom, a methyl radical and an ethyl radical, $R^5$ is an alkylene radical having from 1 to 4 carbon atom(s), v is 0 or an integer and w is 0 or an integer, with the proviso that the radical A contains at least one spacer $—(R^5O)—$, and x is 0 or 1 and y is 0 or 1, with the proviso that the sum $x+y$ is 1 or 2.

4. The organosilicon compound of claim 1, which is an organopolysiloxane of the formula $$A_gR_{3-g}SiO(SiR_2O)_n(SiRAO)_mSiR_{3-g}A_g \quad (III)$$

in which R is selected from the group consisting of monovalent hydrocarbon radicals having from 1 to 18 carbon atom(s) per radical and monovalent halogenated hydrocarbon radicals having from 1 to 18 carbon atom(s) per radical, g is 0 or 1, n is 0 or an integer of from 1 to 1,500, and m is 0 or an integer of from 1 to 100, with the proviso that each molecule contains at least one radical A, where A is a radical of the formula $(H_2C=CR^4CHR^3O(R^5O)_vR^2)_xH_{1-x}C=$ $=CH_{2-y}(R^2(OR^5)_wOCHR^3CR^4=CH_2)_y$ in which $R^2$ is an alkylene radical having from 1 to 4 carbon atom(s), $R^3$ is selected from the group consisting of a hydrogen atom and a methyl radical, $R^4$ is selected from the group consisting of a hydrogen atom, a methyl radical and an ethyl radical, $R^5$ is an alkylene radical having from 1 to 4 carbon atom(s), v is 0 or an integer and w is 0 or an integer, with the proviso that the radical A contains at least one spacer $—(R^5O)—$, and x is 0 or 1 and y is 0 or 1, with the proviso that the sum $x+y$ is 1 or 2.

5. The organosilicon compound containing alkenyl groups of claim 1, wherein the sum of x and y is 1.

6. A process for preparing the organosilicon compound of claim 1, which comprises in a 1st step, reacting an organic compound (1) of the formula pti $(H_2C=CR^4CHR^3O(R^5O)_vR^2)_xH_{1-x}C=CH_{3-y}(R^2(OR^5)_wOCHR^3CR^4=CH_2)_y$ in which $R^2$ is an alkylene radical having from 1 to 4 carbon atom(s), $R^3$ is selected from the group consisting of a hydrogen atom and a methyl radical, $R^4$ is selected from the group consisting of a hydrogen atom, a methyl radical and an ethyl radical, $R^5$ is an alkylene radical having from 1 to 4 carbon atom(s), v is 0 or an integer and w is 0 or an integer, with the proviso that the radical A contains at least one spacer $—(R^5O)—$, and x is 0 or 1 and y is 0 or 1, with the is 1 or 2, with an organosilicon compound (2) containing at least one Si-bonded hydrogen atom in its molecule, in the presence of a catalyst (3) which promotes the addition reaction of Si-bonded hydrogen with an aliphatic multiple bond.

7. The process of claim 6, wherein the organosilicon compound containing alkenyl groups obtained from the 1st step is equilibrated with an organopolysiloxane (4) selected from the group comprising linear organosiloxanes containing terminal triorganosiloxy groups, linear organopolysiloxanes containing terminal hydroxyl groups, cyclic organopolysiloxanes and copolymers comprising diorganosiloxane and monoorganosiloxane units.

8. The process of claim 6, wherein the organosilicon compound (2) having at least one Si-bonded hydrogen atom in its molecule is a silane (2a) of the formula $$HR_dSi(OR^1)_{3-d} \quad (V),$$

in which R is selected from the group consisting of monovalent hydrocarbon radicals having from 1 to 18 carbon atom(s) per radical and monovalent halogenated hydrocarbon radicals having from 1 to 18 carbon atom(s) per radical, $R^1$ is selected from the group consisting of alkyl radicals having from 1 to 8 carbon atom(s) per radical, and alkyl radicals having from 1 to 8 carbon atom(s) per radical which are substituted by one or more ether oxygen atom(s), and d is 0, 1 or 2.

9. The process of claim 6, wherein the organosilicon compound (2) containing at least one Si-bonded hydrogen atom in its molecule is an organopolysiloxane (2b) of the formula $$H_gR_{3-g}SiO(SiR_2O)_n(SiRHO)_mSiR_{3-g}H_g \quad (VI),$$

in which R is selected from the group consisting of monovalent hydrocarbon radicals having from 1 to 18 carbon atom(s) per radical and monovalent halogenated hydrocarbon radicals having from 1 to 18 carbon atom(s) per radical, g is 0 or 1, n is 0 or an integer of from 1 to 1,500, and m is, 0 or an integer of from 1 to 100.

* * * * *

UNITED STATES PATENT AND TRADEMARK OFFICE
CERTIFICATE OF CORRECTION

PATENT NO. : 5,250,647
DATED : October 5, 1993
INVENTOR(S) : Christian Herzig It is certified that error appears in the above-identified patent and that said Letters Patent is hereby corrected as shown below:

In Claim 6, Column 16, Lines 16 and 17, delete

"pti $(H_2C=CR^4CHR^3O(R^5O)_vR^2)_xH_{1-x}C\equiv CH_{3-y}(R^2(OR^5)_wOCHR^3CR^4=CH_2)_y$"

and insert in lieu of

--- $(H_2C=CR^4CHR^3O(R^5O)_vR^2)_xH_{1-x}C\equiv CH_{1-y}(R^2(OR^5)_wOCHR^3CR^4=CH_2)_y$ ---.

In Claim 6, Column 16, line 26, after "with the" insert

--- proviso that the sum $x + y$ ---.

Signed and Sealed this

Thirteenth Day of December, 1994

*Attest:*

BRUCE LEHMAN

*Attesting Officer*  *Commissioner of Patents and Trademarks*